(12) United States Patent
Padgett et al.

(10) Patent No.: US 8,148,145 B2
(45) Date of Patent: Apr. 3, 2012

(54) VIRUS COAT PROTEIN VARIANTS WITH SELF-SUBTRACTING PROPERTIES

(75) Inventors: Hal S. Padgett, Vacaville, CA (US); Fakhrieh S. Vojdani, Davis, CA (US)

(73) Assignee: Novici Biotech, LLC, Vacaville, CA (US)

( * ) Notice: Subject to any disclaimer, the term of this patent is extended or adjusted under 35 U.S.C. 154(b) by 216 days.

(21) Appl. No.: 12/431,622

(22) Filed: Apr. 28, 2009

(65) Prior Publication Data

US 2009/0269808 A1    Oct. 29, 2009

Related U.S. Application Data

(60) Provisional application No. 61/048,525, filed on Apr. 28, 2008.

(51) Int. Cl.
*C12N 15/00* (2006.01)
*C07H 21/02* (2006.01)
*A61K 48/00* (2006.01)

(52) U.S. Cl. .................. 435/320.1; 536/23.1; 514/44

(58) Field of Classification Search ............... 435/320.1; 536/23.1; 514/44
See application file for complete search history.

(56) References Cited

OTHER PUBLICATIONS

Stopar et al. 1996; Local dynamics of the M13 major coat protein in different membrane-mimicking systems. Biochemistry 35:15467-15473.*

\* cited by examiner

*Primary Examiner* — Karen Cochrane Carlson
(74) *Attorney, Agent, or Firm* — Wayne P. Fitzmaurice

(57) ABSTRACT

Herein is described a modified viral vector comprising: a coat protein modified, for example by the addition of a cysteine residue, such that the modified viral vector yields less soluble virus relative to that from an unmodified viral vector upon extraction of plant material infected with the modified viral vector, thereby facilitating purification of a recombinant protein expressed from the modified viral vector. Also described is a method of reducing viral coat protein impurities during purification of a recombinant protein, a method of biocontainment for a recombinant viral vector, and a method of generating virus inoculum for the modified viral vector.

14 Claims, 4 Drawing Sheets

| | Ctrl | 1 | 2 | 3 | 4 | 5 | 6 | 7 | 8 | 9 | 10 | 11 |
|---|---|---|---|---|---|---|---|---|---|---|---|---|
| | no mod | TCA | AC | KNC | AKC | LC | PC | SHC | GCA | DCA | GLC | GC |
| Non-reduced | 2000 | 105 | 200 | 20 | 70 | 110 | 70 | 4 | 80 | 100 | 80 | 125 |
| Reduced | 2000 | 800 | 1500 | 175 | 400 | 650 | 1750 | 300 | 200 | 1000 | 750 | 1250 |

Figure 3

VIRUS COAT PROTEIN VARIANTS WITH SELF-SUBTRACTING PROPERTIES

CROSS-REFERENCE TO RELATED APPLICATIONS

This application claims priority from U.S. Provisional Application No. 61/048,525, filed Apr. 28, 2008. The prior application is hereby incorporated by reference in its entirety.

BACKGROUND OF THE INVENTION

Plant-based recombinant protein manufacturing systems that employ viral expression vector technologies can quickly and inexpensively produce large amounts of high quality proteins for pharmaceutical and other uses. When purifying recombinant proteins produced in plants infected with these virus-based gene expression systems, high concentrations of virus particles and viral coat protein are typically present in the homogenate and subsequent product stream. Removal of these impurities can be time-consuming and costly. Several approaches have been applied to remove virus from plant extracts, including pH and temperature shifts, ultrafiltration, and combinations thereof. However, these strategies are not always compatible with the biochemical properties of the product and, since their efficiencies vary, additional downstream virus removal steps may still be required. With each successive step in a purification process, the quantity of recovered product decreases and the overall costs of the process tend to increase. Removing virus and coat protein impurities at an early stage would be expected to relieve the burden on downstream separation steps and help to control purification costs. Additionally, diminishing the infective potential of the virus would serve as an internal safeguard against accidental release of the recombinant virus into the environment.

BRIEF SUMMARY OF THE INVENTION

To address the problem of virus removal from plant extracts, we have developed a robust approach based on a modification of the coat protein of a tobamovirus viral expression vector with a carboxy-terminal cysteine residue situated in a context that allows it to participate in intermolecular disulfide bond formation. This approach can bring about a reduction of virus and coat protein content in the product stream by over an order of magnitude. Moreover, the reduction in virus content is achieved while maintaining the performance advantages of the viral vector manufacturing platform that include speed, simplicity and high-level product accumulation.

Beyond the advantages brought to the manufacturing process by this approach, we have found that by reducing the solubility of virus in plant extracts, the potential for transmission of the virus can be minimized without compromising the performance of the viral expression vector. Such modifications may be useful as a biological containment feature that can be applied in conjunction with existing virus management strategies to lessen the escape potential of recombinant viral vectors. Escape of recombinant virus is an important consideration in the relatively unconfined growing conditions of open fields where multiple complementary layers of containment, both physical and biological, are needed to safeguard against accidental release of virus into the environment.

Current methods for disposal of tobacco waste containing recombinant virus include spreading the material onto the fields from which the plants were harvested. Those fields already contain virus associated with residual plant matter left in the field at harvest. Stringent tests performed over the course of a number of years have shown that very little if any virus persists in soils that are currently in use for large-scale field grown tobacco manufacturing. Nevertheless, in light of a recent finding that tobacco mosaic virus (TMV) can persist in certain soil types for at least 18 months under long-term field conditions (Gülser C, Yllmaz N K, Candemir F, Environ Monit Assess. Jan. 12, 2008), taking additional steps to ensure that the infectious potential of residual virus in the field is minimized may be a practical and inexpensive way to enhance the biological containment level of these otherwise safe and cost-effective manufacturing systems.

These and other features, aspects and advantages of the present invention will become better understood with reference to the following drawings, description and claims.

BRIEF DESCRIPTION OF THE DRAWINGS

FIG. 3. Average numbers of infection sites as judged by green fluorescent protein (GFP) fluorescence at two days post inoculation. Two leaves were inoculated with extracts of plants infected with the unmodified control virus (Ctrl) or the different modified constructs (numbered) with C-terminal fusions of the cysteine-containing amino acid sequences as shown in the second row.

DETAILED DESCRIPTION OF THE INVENTION

Figure 1:
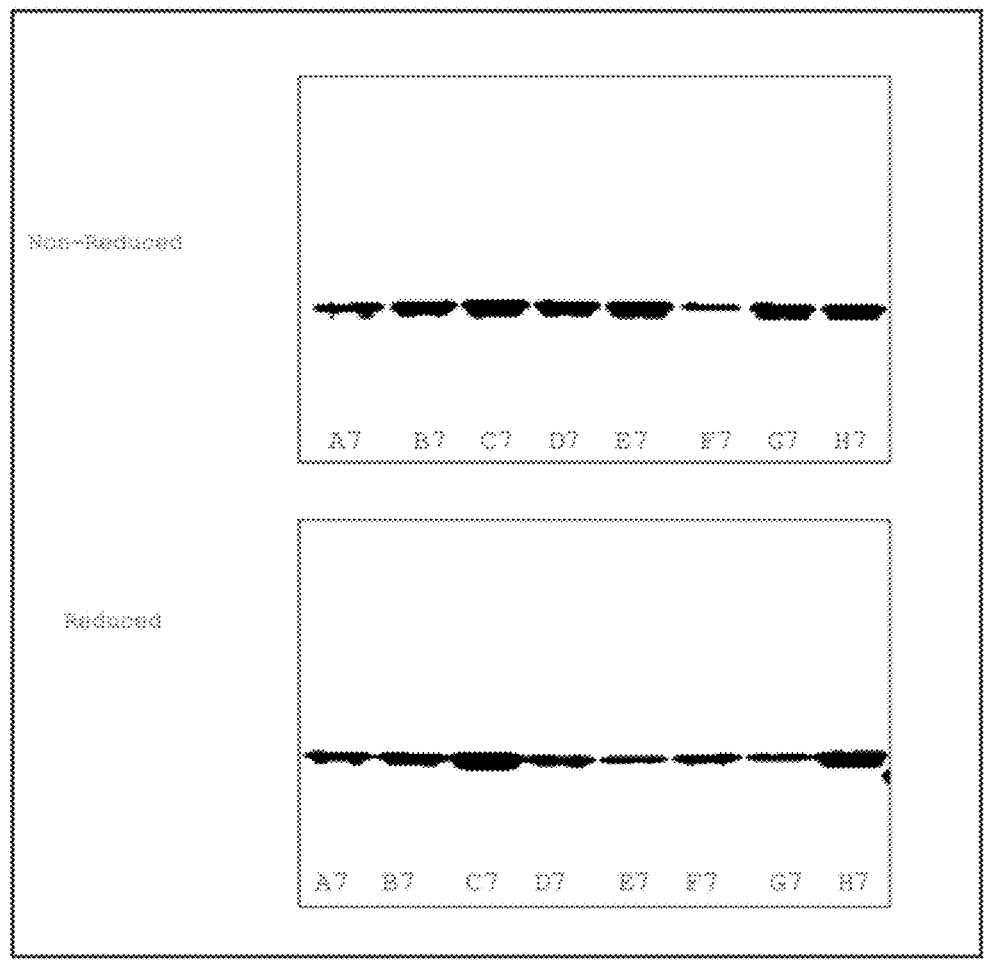
FIG. 1. Yields of purified IFN product from different cysteine modified coat protein clones in the presence or absence of reducing agent. Coomassie-stained polyacrylamide gel electrophoresis (PAGE) gels showing interferon (IFN) proteins extracted and purified with nickel resin from a representative subset of clones from the cysteine-modified coat protein library under non-reducing (top) and reducing conditions (bottom). Sample C7 is derived from the unmodified coat protein control.
Figure 2:
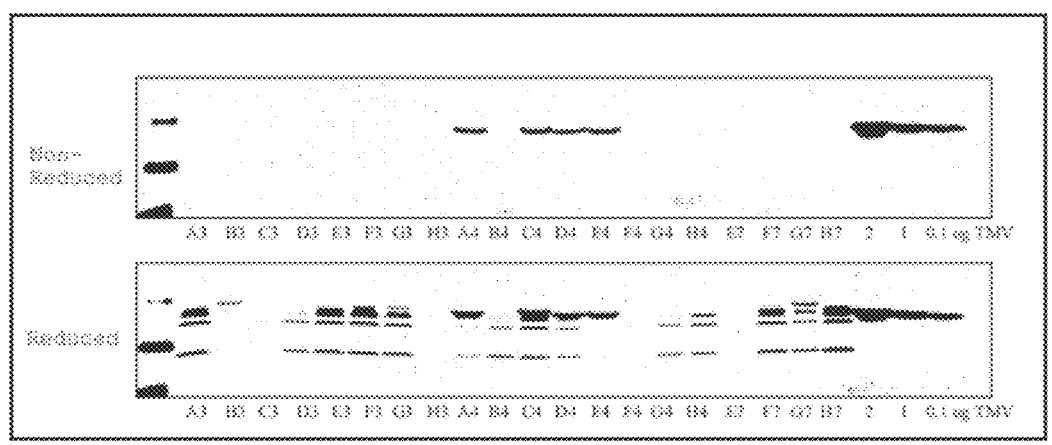
FIG. 2. Coomassie stained PAGE gels of polyethylene glycol (PEG) precipitated virus samples from a representative subset of clones from the cysteine-modified coat protein library. The top and bottom panels show samples extracted and PEG purified under non-reducing and reducing conditions, as labeled. The three lanes at the right of each panel represent different quantities of purified TMV control protein as indicated. All the samples shown are derived from constructs encoding a cysteine at or near their C-terminus of the coat protein with the exception of A4, C4, D4, and E4.

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Various inventive features are described below that can each be used independently of one another or in combination with other features. However, any single inventive feature may not address any of the problems discussed above or may only address one of the problems discussed above. Further, one or more of the problems discussed above may not be fully addressed by any of the features described below.

Development of these cysteine-modified viral vectors was begun by creating a library of coat protein genes modified to incorporate a cysteine residue at or near the carboxy terminus of the coat protein (cp) molecule along with a short random amino acid sequence. Because the most suitable amino acid sequence context and length could not be easily predicted, a randomized library of viral vector-based candidate clones was constructed that consisted of six different configurations of Cys, including cp-X-Cys, cp-XX-Cys, cp-XXX-Cys, cp-X-Cys-X, cp-XX-Cys-X, cp-XXX-Cys-X where X corresponds to any amino acid. The constructs were made by polymerase chain reaction (PCR) amplification of the cp gene with oligonucleotides randomized in the corresponding codon positions with NNK (as read in the sense strand) where N=G, A, T, or C, and K=G or T.

PCR products encoding to the six different Cys configurations were isolated, pooled, and subcloned between the AvrII and KpnI sites of pDN-15-a2aHK, the plasmid encoding the viral vector that contains the gene encoding IFN alpha2aHK, a human interferon (IFN) that is C-terminally tagged with 6 histidines and an endoplasmic reticulum retention sequence. With this vector, monitoring of interferon protein accumulation in the resulting library of variants could be performed using nickel affinity resin chromatography followed by protein quantitation to identify those variants that had not been compromised in their ability to produce recombinant protein.

After transformation of the ligated library into *Escherichia coli,* 94 individual colonies were picked, grown in liquid media, and plasmid extractions were performed. Each clone was transcribed to produce infectious RNA that was inoculated onto leaves of *Nicotiana benthamiana* plants along with the two replicates of a wild-type control.

Successful variants were selected from the library based on a number of criteria that were primarily related to the fitness level of the virus and its ability to perform in plants at or near the level of the parent vector. These criteria comprised the ability to spread systemically, lack of induction of severe symptoms, and accumulation of levels of protein product similar to the level of the parental controls. After identifying candidates that had maintained these qualities, the amount of soluble coat protein remaining after plant homogenization and centrifugation of the extract was considered. In addition, the overall length of the added amino acid sequences and the recoverability of virus when extracted in the presence of reducing agent were also examined.

Of the 94 candidates that were inoculated, 54 exhibited levels of systemic spread comparable to the parent vector. As expected, some modifications to the coat protein apparently interfered with virion assembly or trafficking within the plant, making them less suitable for use in the context of a viral vector system. Also, the process of generating the library involved PCR, which could have introduced deleterious mutations in the region that was amplified. After confirmation by repeat inoculation, any such non-systemic members of the library were excluded from further analysis.

At about eight days post-inoculation, infected leaf tissue was harvested from plants infected with each of the 54 candidates showing systemic infection. Harvested tissue was split into two portions and processed by extraction under reducing and non-reducing conditions. The homogenates were clarified by centrifugation at 11,000 rpm in a JA-14 rotor and samples were taken for direct polyacrylamide gel electrophoresis (PAGE) analysis. The remainder of each sample was subjected to nickel resin affinity chromatography to capture the expressed 6His-IFN alpha 2a and the resulting samples were analyzed by PAGE (for example see FIG. 1). Of the 54 plants showing systemic symptoms, 32 had levels of the IFN protein that were at least 50% of the control level. Slightly less IFN protein was recovered, on average, from the samples extracted under reducing conditions, probably because of the influence of the beta-mercaptoethanol on the efficiency of the Ni-resin chromatography step.

A portion of each plant extract was also processed with two rounds of PEG precipitation to isolate any soluble virus present in the sample. These samples were analyzed by PAGE as well as by spectrophotometric analysis. Gel analysis of the PEG precipitated virus samples showed that for most, if not all, of the different clones containing a cysteine-modified coat protein, less coat protein was present in extracts made under non-reducing conditions than under reducing conditions (for example see FIG. 2), suggesting that oxidative cross-linking and precipitation of the cysteine-modified coat proteins was taking place under non-reducing conditions. Approximately the same amount of virus was obtained under both sets of conditions for the unmodified coat protein controls. Interestingly, several of the clones encoding modified coat proteins did not show any difference from the control, suggesting that cysteine-mediated cross-linking doesn't necessarily occur with all coat proteins containing a cysteine near the C-terminus.

For each of the 32 virus constructs with acceptable levels of product accumulation, the coat protein gene was sequenced. In ten of the clones, the added C-terminal sequences were four or more amino acids in length. These were eliminated from further analysis out of concern that the larger amino acid additions could cause undetermined deleterious effects. Of the remaining 22 candidates, DNA sequence chromatograms of three of the corresponding DNA clones contained ambiguities. In-frame stop codons were found near the C-terminus of three others.

In the reducing environment of the intact plant cell cytoplasm, disulfide bond formation between surface Cys residues on the modified viruses is minimized, helping to maintain the solubility of the virus. Upon disruption of cells under oxidizing (or at least not strongly reducing) conditions, oxidative cross linking of virus particles through their surface Cys residues can then cause virus aggregation and formation of precipitates that can be removed by centrifugation or filtration. Of the 16 candidates that had passed the selection criteria listed above, four showed levels of coat protein in the non-reducing extracts that were comparable to, or only somewhat less than, the control. The remaining 12 showed very low or undetectable levels of coat protein when extracted under non-reducing conditions (not shown).

These 12 candidates were then subjected to a series of second-tier screens in order to further characterize and rank them. In each of the 12 constructs, the interferon gene was replaced by the gene encoding GFP with a C-terminal 6-histidine tag. The resulting 12 GFP constructs were inoculated in duplicate onto *N. benthamiana* and fluorescence was monitored to follow the development and spread of the virus infection in the plants. After about eight days, the plants were photographed under ultraviolet (UV) light to record the GFP fluorescence, then harvested and individually homogenized and centrifuged under non-reducing conditions. The duplicate extracts were then analyzed to quantitate the levels of GFP protein and residual coat protein by gel densitometry. All 12 clones produced the GFP protein product at levels comparable to the control virus. The level of residual coat protein present in the extracts ranged from roughly half concentration seen in the control to undetectable levels for one of the constructs.

Eleven of these 12 GFP constructs were also analyzed for virus infectivity after extraction under non-reducing conditions versus extraction under reducing conditions with 0.5% β-mercaptoethanol. These crude extracts were clarified by brief centrifugation to remove large debris, and the supernatants were each diluted with an equal volume of FES, an abrasive solution used to facilitate inoculation of plants. After rub-inoculation of *N. benthamiana* leaves with each of the resulting samples, leaves were monitored by UV illumination to visualize virus infection sites. For the unmodified virus controls, reducing and non-reducing extracts showed equivalent numbers of infection sites, estimated to be at least 2000 per leaf (FIG. 3), reaching confluence within several days. Of the constructs with cysteine-modified coat proteins, the number of infection sites extracted under non-reducing conditions ranged from roughly 0.02% to 10% of the number seen in the unmodified controls, and generally paralleled the results of the protein concentration data for the clones. Under reducing conditions, the infectivities of the same set of constructs were restored to levels ranging from 10% to 87.5% of wild-type (unmodified) coat protein controls. The increase in infectivity obtained for these clones when extracted under reducing versus non-reducing conditions ranged from 2.5 to 75-fold, with an average of about 15-fold. This experiment showed that the infectivity of the virus could be controlled with reducing agent, presumably by modulating the oxidative status of the cysteines and thus, the solubility of the particles.

Figure 4:
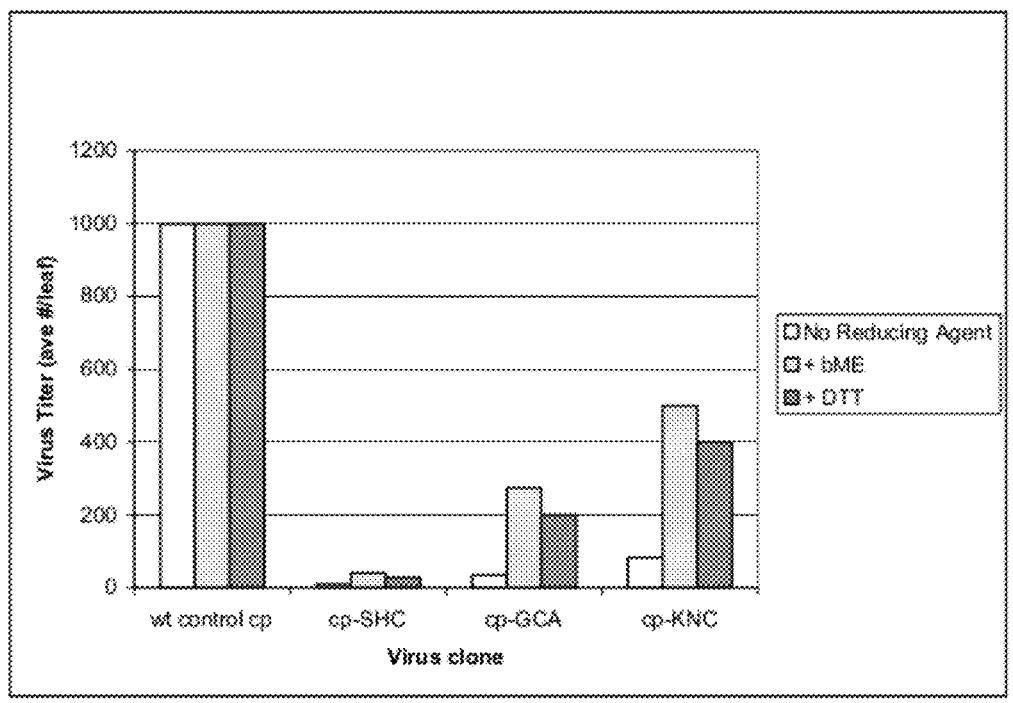
FIG. 4. Reduction of virus titer for cysteine-modified coat proteins (with and without reducing agent). Plants were infected with viral vectors expressing GFP and containing either the wild-type coat protein or the cysteine-modified coat proteins with the C-terminal amino acid sequence of SHC, GCA, or KNC. Plants from each set were homogenized in 100 mM Tris-Cl pH 7.5, 250 mM NaCl, in the presence or absence of beta-mercaptoethanol (bME) (71 mM final) or dithiothreitol (DTT) (2.7 mM final). The crude extracts were then mixed with an equal volume of FES and inoculated to *Nicotiana benthamiana* leaves. 48 hours after inoculation, infection sites were counted as GFP spots under ultraviolet (UV) light, and the average number of spots per leaf was plotted.

A confirmation experiment for three of the cysteine-modified viral vectors is shown in FIG. 4. The bar graph shows the viral titer under reducing and non-reducing conditions from extracts of plants that were infected with viral vectors expressing GFP and containing either the wild-type coat protein or the cysteine-modified coat proteins with the C-terminal amino acid sequence of SHC, GCA, or KNC. Again a several-fold increase in infectivity is obtained for these clones when extracted under reducing versus non-reducing conditions.

An embodiment of the instant invention is a method of generating virus inoculum for a viral vector comprising: modifying the coat protein gene of a viral vector to encode a cysteine residue at or near the 3' end of the gene such that the coat protein expressed from the gene is less soluble than unmodified coat protein under non-reducing conditions to form a modified viral vector; introducing a gene encoding a recombinant protein into the modified viral vector; infecting a plant with the modified viral vector containing a gene encoding a recombinant protein resulting in infected plant material; and isolating virus from the infected plant material under reducing conditions to generate virus inoculum.

Another embodiment of this invention is the development of a viral expression vector system that yields less soluble virus upon extraction to facilitate downstream purification. By minimizing the amount of virus present in extracts, this system also presents a practical approach to reduce virus transmissibility, and represents a potent biocontainment strategy. Moreover, with specific treatments, the virus can be selectively recovered in soluble form to obtain infectious material to use as inoculum for large-scale plant inoculations.

In these experiments it was found that coat proteins with different cysteine-containing amino acid sequences behave differently in the various assays that were performed. Only a few candidates of the initial library of clones displayed the desired combination of properties. It is expected that analysis of additional candidates from this library as well as from other combinatorial libraries would result in the identification of additional clones with unique properties. These properties can be identified through the use of properly designed screens that can discern the particular characteristics that are of interest. Experiments reported above describe the C-terminal addition of amino acid sequences containing cysteine to the coat protein of a tobamovirus-based plant viral vector. Through positioning of the cysteine-containing sequences or other sequences that can mediate intermolecular interactions at other positions of the coat protein (e.g., N-terminal or internal on a surface-exposed loop of the coat protein), it is possible to identify variants with similar properties to those identified for C-terminal modifications to coat protein. Successful variants are selected based on a number of criteria that are primarily related to the fitness level of the virus and its ability to perform in plants at or near the level of the parent (unmodified) vector. These criteria comprise the ability to spread systemically, lack of induction of severe symptoms, and accumulation of levels of protein product similar to the level of the parental controls. After identifying candidates that maintain these vector-related qualities, the amount of soluble coat protein remaining after plant homogenization and centrifugation of the extract is considered. In addition, the overall length of the added amino acid sequences and the recoverability of virus when extracted in the presence of reducing agent are also examined. Hence, in like manner to the screening process used for the C-terminally modified coat protein vectors described, N-terminal or internal modifications of the coat protein with desirable properties of acceptable vector performance and reduced coat protein solubility can be identified.

Another embodiment of the instant invention is a method of reducing viral coat protein impurities during purification of a recombinant protein comprising: modifying the coat protein gene to form a first viral vector such that a modified coat protein expressed from the gene is less soluble than unmodified coat protein under non-reducing conditions; introducing a gene encoding a recombinant protein into the first viral vector; infecting a first plant with the first viral vector containing the gene encoding a recombinant protein; extracting proteins from the infected first plant to form a first crude extract; and purifying the recombinant protein from the first crude extract under non-reducing conditions such that the amount of viral coat protein impurity is less relative to a second crude extract made by infecting a second plant with a second viral vector encoding the unmodified coat protein.

Another embodiment of the instant invention is a modified viral vector comprising: a modified coat protein gene such that the modified viral vector yields less soluble virus relative to that from an unmodified viral vector upon extraction of plant material infected with the modified viral vector, thereby facilitating purification of a recombinant protein expressed from the modified viral vector.

Another embodiment of the instant invention is a method of biocontainment for a recombinant viral vector comprising: modifying the coat protein gene to form a first viral vector such that the coat protein expressed from the gene is less soluble than unmodified coat protein under non-reducing conditions; introducing a gene encoding a recombinant protein into the first viral vector; and infecting a plant with the first viral vector containing a gene encoding a recombinant protein, resulting in infected plant material such that a crude extract of the plant material has less infectious virus than a crude extract made using a second viral vector encoding the unmodified coat protein.

It is contemplated that vectors derived from viruses other than tobamoviruses could benefit from the approach taught herein.

It should be understood, of course, that the foregoing relates to exemplary embodiments of the invention and that modifications may be made without departing from the spirit and scope of the invention as set forth in the following claims.

What is claimed is:

1. A viral vector comprising: a modified coat protein gene such that the coat protein modified viral vector yields less soluble virus relative to that from an unmodified viral vector upon extraction of plant material infected with the coat protein modified viral vector, said modified coat protein gene encoding an amino acid sequence added on to the carboxy-terminus of a tobamovirus coat protein, and said amino acid sequence selected from the group consisting of TCA, AC, KNC, AKC, LC, PC, SHC, GCA, DCA, GLC, and GC.

2. The viral vector of claim 1 where said amino acid sequence is TCA.

3. The viral vector of claim 1 where said amino acid sequence is AC.

4. The viral vector of claim 1 where said amino acid sequence is KNC.

5. The viral vector of claim 1 where said amino acid sequence is AKC.

6. The viral vector of claim 1 where said amino acid sequence is LC.

7. The viral vector of claim 1 where said amino acid sequence is PC.

8. The viral vector of claim 1 where said amino acid sequence is SHC.

9. The viral vector of claim 1 where said amino acid sequence is GCA.

10. The viral vector of claim 1 where said amino acid sequence is DCA.

11. The viral vector of claim 1 where said amino acid sequence is GLC.

12. The viral vector of claim 1 where said amino acid sequence is GC.

13. A method of reducing viral coat protein impurities during purification of a recombinant protein comprising:

a) modifying a coat protein gene to form a first viral vector such that a modified coat protein expressed from the gene is less soluble than unmodified coat protein under non-reducing conditions, wherein the modified coat protein gene encodes an amino acid sequence added on to the carboxy-terminus of a tobamovirus coat protein, said amino acid sequence selected from the group consisting of TCA, AC, KNC, AKC, LC, PC, SHC, GCA, DCA, GLC, and GC;

b) introducing a gene encoding a recombinant protein into the first viral vector;

c) infecting a first plant with the first viral vector containing the gene encoding a recombinant protein;

d) extracting proteins from the infected first plant to form a first crude extract; and e) purifying the recombinant protein from the first crude extract under non-reducing conditions such that the amount of viral coat protein impurity is less relative to a second crude extract made by infecting a second plant with a second viral vector encoding unmodified coat protein.

14. A method of biocontainment for a recombinant viral vector comprising:

a) modifying a coat protein gene to form a first viral vector such that the coat protein expressed from the gene is less soluble than unmodified coat protein under non-reducing conditions wherein the modified coat protein gene encodes an amino acid sequence added on to the carboxy-terminus of a tobamovirus coat protein, said amino acid sequence selected from the group consisting of TCA, AC, KNC, AKC, LC, PC, SHC, GCA, DCA, GLC, and GC;

b) introducing a gene encoding a recombinant protein into the first viral vector; and c) infecting a plant with the first viral vector containing the gene encoding a recombinant protein, resulting in infected plant material such that a crude extract of the plant material has less infectious virus than a crude extract made using a second viral vector encoding unmodified coat protein.

* * * * *